United States Patent
Reebye et al.

(10) Patent No.: US 12,357,424 B2
(45) Date of Patent: Jul. 15, 2025

(54) SPLINT DEVICE FOR GUIDED SURGICAL ROBOT

(71) Applicants: NEOCIS INC., Miami, FL (US); Uday N. Reebye, Durham, NC (US)

(72) Inventors: Uday N. Reebye, Durham, NC (US); Mauro Fittipaldi, Miami, FL (US); Alon Mozes, Miami Beach, FL (US); Juan Salcedo, Miami, FL (US); David Paul Lustbader, Canton, MA (US); Richard Prentice Boyle, Blacksburg, VA (US)

(73) Assignee: NEOCIS INC., Miami, FL (US)

( * ) Notice: Subject to any disclaimer, the term of this patent is extended or adjusted under 35 U.S.C. 154(b) by 293 days.

(21) Appl. No.: 17/915,863

(22) PCT Filed: Mar. 30, 2021

(86) PCT No.: PCT/IB2021/052651
§ 371 (c)(1),
(2) Date: Sep. 29, 2022

(87) PCT Pub. No.: WO2021/198923
PCT Pub. Date: Oct. 7, 2021

(65) Prior Publication Data
US 2023/0131343 A1      Apr. 27, 2023

Related U.S. Application Data

(60) Provisional application No. 63/002,074, filed on Mar. 30, 2020.

(51) Int. Cl.
*A61C 5/00*       (2017.01)
*A61B 34/20*      (2016.01)
(Continued)

(52) U.S. Cl.
CPC .............. *A61C 5/007* (2013.01); *A61B 34/20* (2016.02); *A61B 34/30* (2016.02); *A61C 1/082* (2013.01);
(Continued)

(58) Field of Classification Search
CPC ......... A61C 5/007; A61C 1/082; A61B 34/20; A61B 34/30; A61B 2034/2065; A61B 2090/3966
See application file for complete search history.

(56) References Cited

U.S. PATENT DOCUMENTS

| | | | |
|---|---|---|---|
| 6,269,148 B1 | 7/2001 | Jessop et al. | |
| 8,831,322 B2 * | 9/2014 | Abboud | A61B 6/51 382/128 |

(Continued)

FOREIGN PATENT DOCUMENTS

| | | |
|---|---|---|
| JP | 2017-509450 | 4/2017 |
| JP | 2018-110841 | 7/2018 |

(Continued)

*Primary Examiner* — Nicholas D Lucchesi
(74) *Attorney, Agent, or Firm* — Womble Bond Dickinson (US) LLP

(57) ABSTRACT

A splint device for guided robotic surgery, includes an arcuate splint body having first and second ends and opposing concave and convex surfaces. The splint body defines a plurality of holes spaced apart between the first and second ends, with each hole extending between the concave and convex surfaces. A tracking portion is engaged with the convex surface of the splint body between the first and second ends such that at least one of the holes is disposed between the tracking portion and each of the first and second ends. The tracking portion extends outwardly from the convex surface and has a kinematic mount engaged therewith.

10 Claims, 6 Drawing Sheets

Figure 1A:
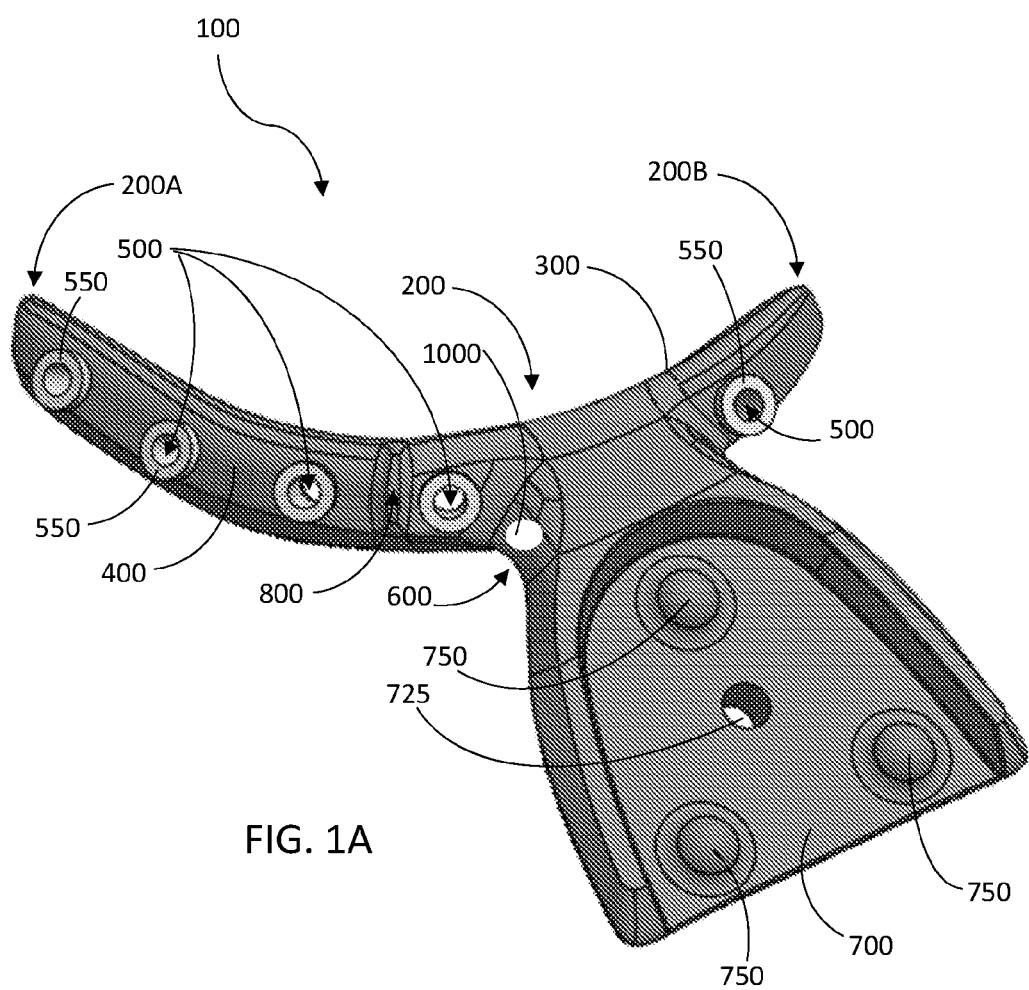

(51) Int. Cl.
    *A61B 34/30*     (2016.01)
    *A61C 1/08*     (2006.01)
    *A61B 17/00*     (2006.01)
    *A61B 90/00*     (2016.01)

(52) U.S. Cl.
    CPC .............. *A61B 2017/00725* (2013.01); *A61B 2034/2065* (2016.02); *A61B 2090/3966* (2016.02); *A61B 2090/3983* (2016.02)

(56) References Cited

U.S. PATENT DOCUMENTS

| | | | |
|---|---|---|---|
| 11,389,304 B1* | 7/2022 | Nikou | G16H 50/20 |
| 2005/0106529 A1* | 5/2005 | Abolfathi | A61C 9/0006 |
| | | | 433/41 |
| 2005/0228256 A1 | 10/2005 | Labadie et al. | |
| 2006/0201520 A1* | 9/2006 | Christensen, III | A61C 9/0006 |
| | | | 128/860 |
| 2006/0281991 A1 | 12/2006 | Fitzpatrick et al. | |
| 2009/0209852 A1 | 8/2009 | Mate et al. | |
| 2013/0009657 A1 | 1/2013 | Su et al. | |
| 2014/0186793 A1* | 7/2014 | Kurti, Jr. | A61B 5/0075 |
| | | | 600/407 |
| 2014/0343395 A1* | 11/2014 | Choi | A61B 5/4851 |
| | | | 600/409 |
| 2015/0133956 A1 | 5/2015 | Dayan et al. | |
| 2016/0278875 A1 | 9/2016 | Crawford et al. | |
| 2016/0317108 A1* | 11/2016 | Dekel | A61B 6/12 |
| 2016/0367343 A1 | 12/2016 | Mozes et al. | |
| 2017/0105802 A1 | 4/2017 | Taraschi et al. | |
| 2017/0265974 A1 | 9/2017 | Morales et al. | |
| 2017/0348055 A1 | 12/2017 | Salcedo et al. | |
| 2020/0038160 A1* | 2/2020 | Hornung | A61C 9/004 |
| 2020/0146790 A1* | 5/2020 | Marshall | A61C 19/045 |
| 2020/0237265 A1 | 7/2020 | Jaisson | |

FOREIGN PATENT DOCUMENTS

| | | | | |
|---|---|---|---|---|
| JP | 2019-506929 | | 3/2019 | |
| WO | WO-2006094156 A2 * | | 9/2006 | ............ A61B 34/20 |
| WO | WO 2018/158551 | | 9/2018 | |
| WO | WO-2021198919 A1 * | | 10/2021 | ............ A61B 34/20 |

* cited by examiner

SPLINT DEVICE FOR GUIDED SURGICAL ROBOT

CROSS-REFERENCE TO RELATED APPLICATIONS

This application is a national stage filing under 35 U.S.C. 371 of PCT/IB2021/052651, filed Mar. 30, 2021, which International Application was published by the International Bureau in English on Oct. 7, 2021, as WO 2021/198923, and application claims priority from U.S. Provisional Application No. 63/002,074, filed on Mar. 30, 2020, which applications are hereby incorporated in their entirety by reference in this application.

BACKGROUND

Field of the Disclosure

The present application relates to surgical robots and associated guidance systems and, more particularly, to a splint device for forming a fiducial marker and/or a tracking marker for the guidance system of a surgical robot in instances of a fully or partially edentulous patient.

Description of Related Art

Robotic systems are being increasingly implemented in surgical applications. One such example involves a surgical robot used in dental surgery. Such robots are often associated with a guidance system used to guide the surgical instrument implemented by the surgical robot. The guidance system may also be configured to be involved in the surgical pre-planning process, whether by being involved in gathering and/or analyzing patient data, and planning the surgical procedure, or by relying upon pre-planning data to guide the surgical instrument to conduct the surgical procedure.

In particular surgical procedures, some surgical robotic systems rely upon a fixed reference point associated with the patient's body for guiding the surgical robot. That is, some such surgical robotic systems define a frame of reference with respect to the patient's body so as to account or otherwise compensate for movements or motion of the patient during the procedure, whether during pre-planning or during the actual surgical procedure itself. This reference point must also be repeatable such that multiple engagements/disengagements (i.e., periods between pre-planning and the actual surgical procedure) do not change the frame of reference implemented by the surgical robot or the guidance system associated therewith.

In particular instances, the reference point (or the connection between the guidance system and the patient to define that reference point) implemented by the guidance system for the surgical robot may be accomplished through, for example, an optical modality, a mechanical modality, an acoustic modality, or other suitable and appropriate tracking/guiding modality, or combination thereof. In some modalities, particularly used in dental surgery applications, one mechanical modality for forming the reference point (i.e., a "fiducial marker") may be accomplished, for example, by attaching/securing a rigid element to the head/teeth of the patient. Such a rigid element, in some instances, may be referred to as and may comprise a splint. Such a splint may generally include, for instance, a retainer portion that grips one or more of the teeth (i.e., by way of an adhesive substance, such as an acrylic material applied between the retainer portion and the teeth), a mounting portion (i.e., mounting arm) that connects the retainer portion to a separate kinematic mount, and the kinematic mount, itself, which may comprise an attachment point for a tracking portion associated with the guidance system for the surgical robot (i.e., wherein, for instance, reflective markers may be mounted to the attachment point for optical tracking of the fiducial marker, or the attachment point may include a securing site for forming a mechanical connection therewith for mechanical tracking of the fiducial marker, or the attachment point may otherwise be configured to receive an appropriate element associated with any other suitable tracking arrangement for the fiducial marker).

In such instances, it may be preferable for the retainer portion to be as rigid as possible (i.e., the structure of the retainer itself, as well as the fixation thereof to the teeth of the patient) throughout the surgical procedure. However, it may also be preferable for the retainer portion to be readily removable when the surgical procedure is complete. In some instances, it may be preferable for the splint to be reproducibly removed and replaced, for example, between the pre-planning procedure (i.e., a CT scan) which may occur on one day (when the splint must be in place so the fiducial marker(s) associated therewith are captured in the scan), and the surgical procedure may occur on another day (wherein the surgical procedure requires the splint to be in place for tracking/guiding the surgical procedure). In other instances, it may be preferable that a single splint configuration be usable or adaptable across a wide population of patients, for example, as a universal fit (size) device. In addition, it would be desirable for such a splint to be readily applicable to fully or partially edentulous patients (i.e., patients not having sufficient teeth or teeth structure capable of supporting the application of a conventional splint thereto). Since such a splint device would not be reliant upon the patient having teeth or sufficient teeth structure for the application thereof, it would also be desirable for the splint device to be applicable to other parts of the patient to facilitate other types of guided robotic surgery. Further, it may be desirable to have a minimum of separate components of the splint, or if separate components are included, that such separate components are integrated into or are firmly and securely affixed as part of the overall splint assembly. In some instances, it may be desirable for the splint to be re-usable for the particular patient.

As such, there exists a need for a splint device for forming a fiducial marker for the guidance system of a surgical robot used, for example, in dental surgery, and particularly for fully or partially edentulous patients in dental surgery, or other types of surgery, which addresses these and other limitations of prior art devices.

SUMMARY OF THE DISCLOSURE

The above and other needs are met by aspects of the present disclosure which, in one particular aspect, provides a splint device for guided robotic surgery. Such a device comprises an arcuate splint body having first and second ends and opposing concave and convex surfaces. The splint body defines a plurality of holes spaced apart between the first and second ends, with each hole extending between the concave and convex surfaces. A tracking portion is engaged with the convex surface of the splint body between the first and second ends such that at least one of the holes is disposed between the tracking portion and each of the first and second ends. The tracking portion extends outwardly from the convex surface and has a kinematic mount engaged therewith.

The present disclosure thus includes, without limitation, the following example embodiments:

Example Embodiment 1: A splint device for guided robotic surgery, said device comprising an arcuate splint body having first and second ends and opposing concave and convex surfaces, the splint body defining a plurality of holes spaced apart between the first and second ends, each hole extending between the concave and convex surfaces; and a tracking portion engaged with the convex surface of the splint body between the first and second ends such that at least one of the holes is disposed between the tracking portion and each of the first and second ends, the tracking portion extending outwardly from the convex surface and having a kinematic mount engaged therewith.

Example Embodiment 2: The device of any preceding or subsequent example embodiment, or combinations thereof, wherein each hole is arranged to receive a sleeve therein.

Example Embodiment 3: The device of any preceding or subsequent example embodiment, or combinations thereof, wherein the sleeve is comprised of a metallic material or a ceramic material.

Example Embodiment 4: The device of any preceding or subsequent example embodiment, or combinations thereof, wherein the sleeve is arranged as a drill guide or a fastener guide.

Example Embodiment 5: The device of any preceding or subsequent example embodiment, or combinations thereof, wherein the kinematic mount is integrally formed with the tracking portion.

Example Embodiment 6: The device of any preceding or subsequent example embodiment, or combinations thereof, comprising a separability provision extending across the splint body between adjacent holes, wherein the separability provision is arranged to be severable so as to facilitate adjustability of a length of the splint body.

Example Embodiment 7: The device of any preceding or subsequent example embodiment, or combinations thereof, wherein the separability provision comprises a reduced section thickness of the splint body between adjacent holes.

Example Embodiment 8: The device of any preceding or subsequent example embodiment, or combinations thereof, comprising a fiducial marker element received by a depression defined by an outer surface of the splint body or the tracking portion, the fiducial marker element being received in a predetermined disposition relative to the kinematic mount.

Example Embodiment 9: The device of any preceding or subsequent example embodiment, or combinations thereof, wherein the fiducial marker element is spherical and the depression is hemispherical or an elongate concave channel arranged to receive the spherical fiducial marker element.

Example Embodiment 10: The device of any preceding or subsequent example embodiment, or combinations thereof, comprising a tool calibration provision engaged with the splint body or the tracking portion, the tool calibration provision being disposed in a predetermined disposition relative to the kinematic mount.

Example Embodiment 11: The device of any preceding or subsequent example embodiment, or combinations thereof, wherein the concave surface of the splint body is arranged to conform to a mandibular curvature or a maxillary curvature.

These and other features, aspects, and advantages of the present disclosure will be apparent from a reading of the following detailed description together with the accompanying drawings, which are briefly described below. The present disclosure includes any combination of two, three, four, or more features or elements set forth in this disclosure, regardless of whether such features or elements are expressly combined or otherwise recited in a specific embodiment description herein. This disclosure is intended to be read holistically such that any separable features or elements of the disclosure, in any of its aspects and embodiments, should be viewed as intended, namely to be combinable, unless the context of the disclosure clearly dictates otherwise.

It will be appreciated that the summary herein is provided merely for purposes of summarizing some example aspects so as to provide a basic understanding of the disclosure. As such, it will be appreciated that the above described example aspects are merely examples and should not be construed to narrow the scope or spirit of the disclosure in any way. It will be appreciated that the scope of the disclosure encompasses many potential aspects, some of which will be further described below, in addition to those herein summarized. Further, other aspects and advantages of such aspects disclosed herein will become apparent from the following detailed description taken in conjunction with the accompanying drawings which illustrate, by way of example, the principles of the described aspects.

BRIEF DESCRIPTION OF THE SEVERAL VIEWS OF THE DRAWING(S)

Figure 1B:
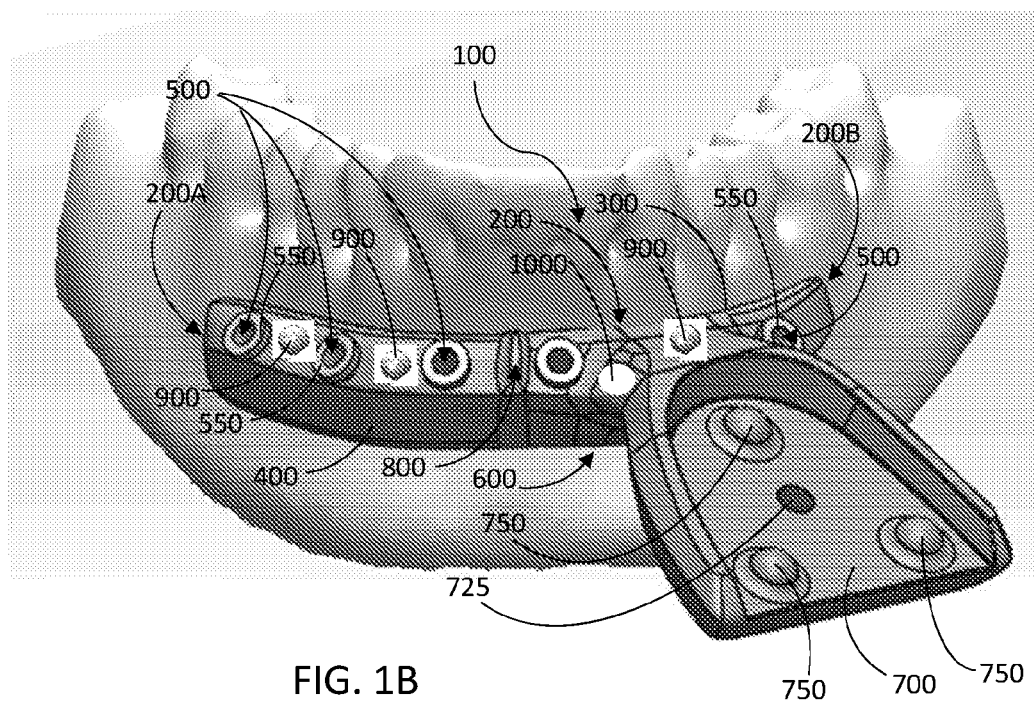
Figure 2A:
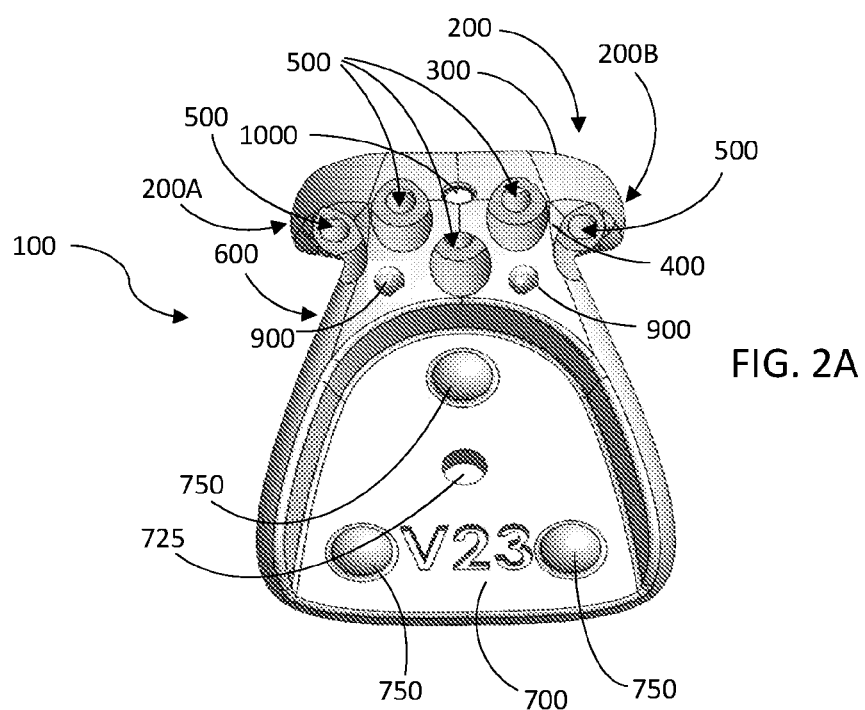
Figure 2B:
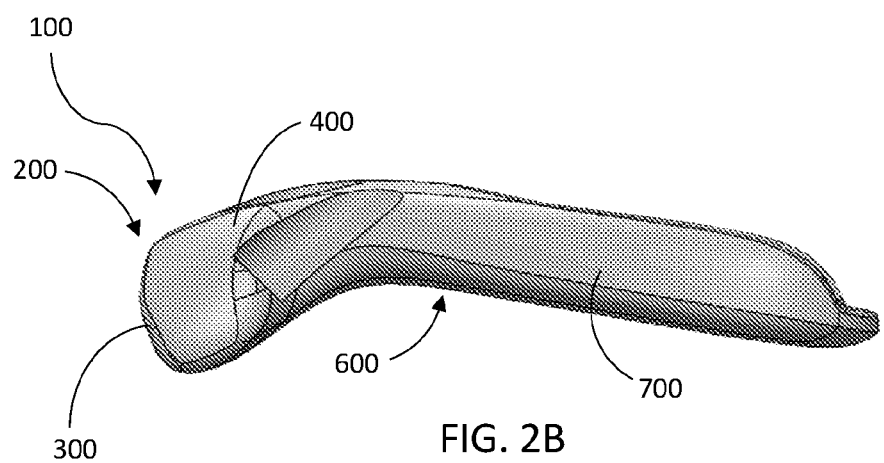
Figure 2C:
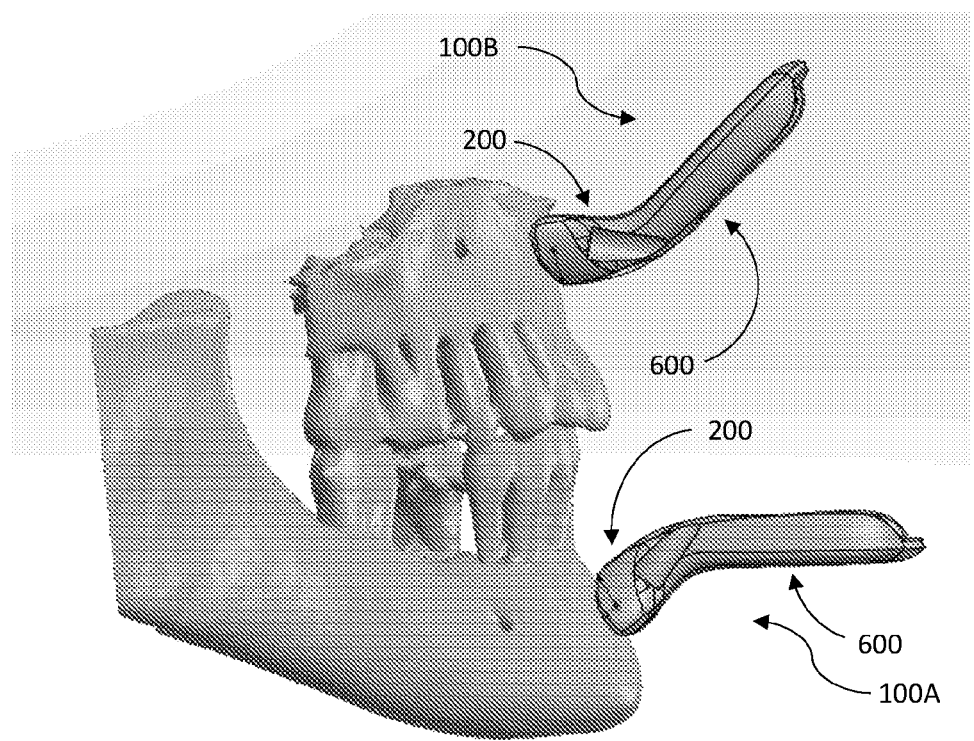
Figure 3A:
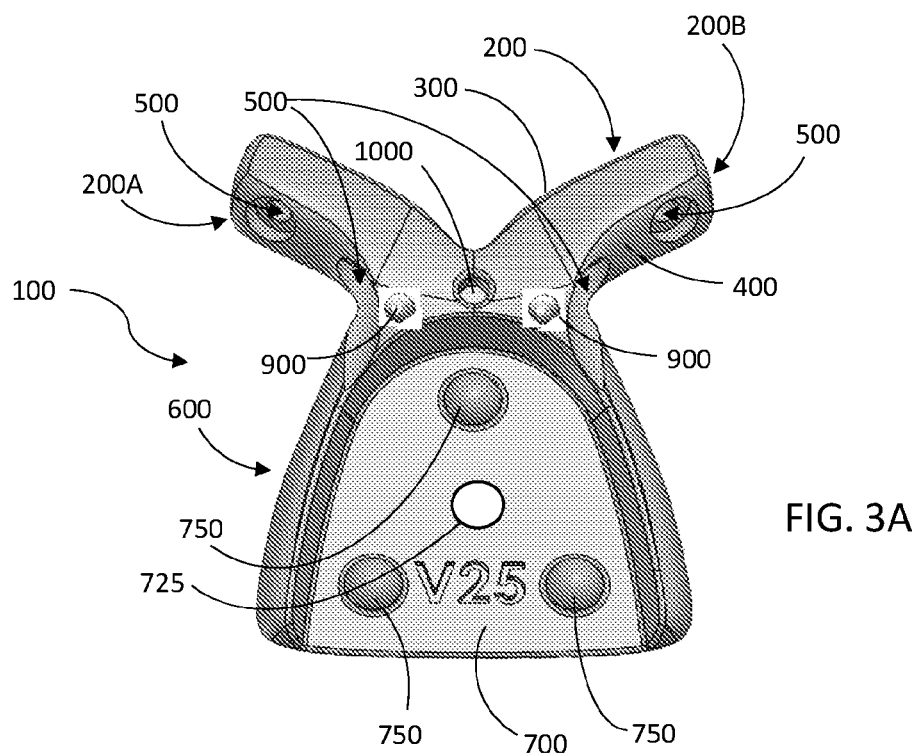
Figure 3B:
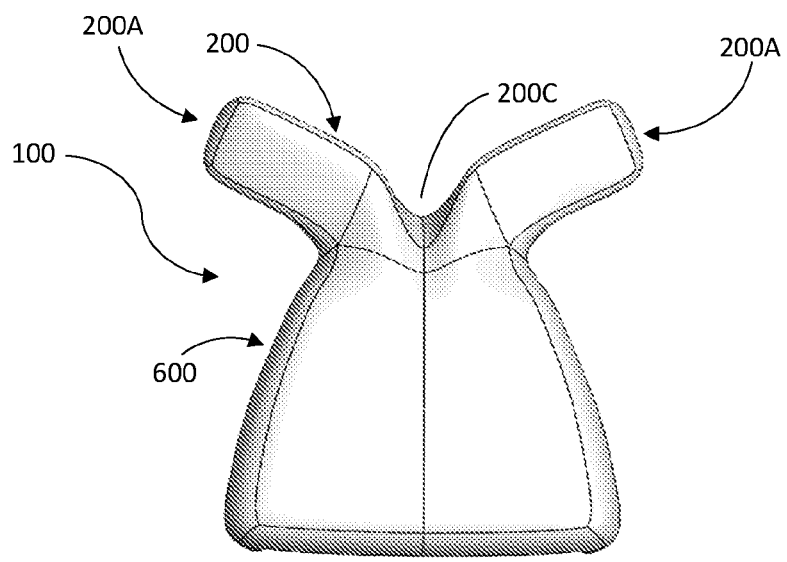
Figure 3C:
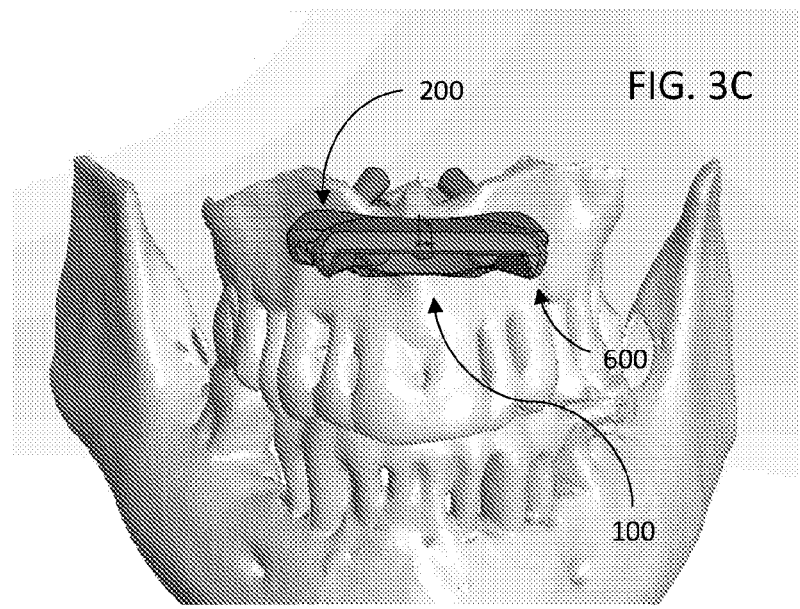
Figure 3D:
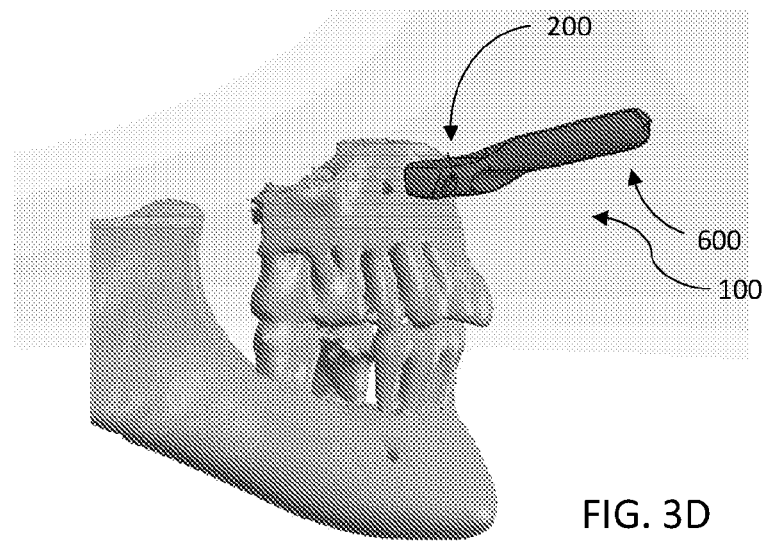

Having thus described the disclosure in general terms, reference will now be made to the accompanying drawings, which are not necessarily drawn to scale, and wherein:

FIGS. 1A and 1B schematically illustrate different perspective views of a splint device applicable, for example, to fully or partially edentulous patients and arranged to provide a fiducial marker and/or a tracking marker for a guidance system for a surgical robot, according to one aspect of the present disclosure;

FIGS. 2A and 2B schematically illustrate a top view and a side profile view of a splint device applicable, for example, to a medial portion of a maxilla or mandible of a fully or partially edentulous patients and arranged to provide a fiducial marker and/or a tracking marker for a guidance system for a surgical robot, according to another aspect of the present disclosure;

FIG. 2C schematically illustrates a splint device according to the aspect of the disclosure shown in FIGS. 2A and 2B, wherein a first one of such a splint device is applied to a mandible and a second one of such a splint device is inverted and applied to a maxilla;

FIGS. 3A and 3B schematically illustrate a top view and a bottom view of a splint device applicable, for example, to a medial portion of a maxilla of a fully or partially edentulous patients and arranged to provide a fiducial marker and/or a tracking marker for a guidance system for a surgical robot, according to still another aspect of the present disclosure; and FIGS. 3C and 3D schematically illustrate a splint device according to the aspect of the disclosure shown in FIGS. 3A and 3B, wherein one such splint device is applied to a maxilla.

DETAILED DESCRIPTION OF THE DISCLOSURE

The present disclosure now will be described more fully hereinafter with reference to the accompanying drawings, in which some, but not all aspects of the disclosure are shown. Indeed, the disclosure may be embodied in many different forms and should not be construed as limited to the aspects set forth herein; rather, these aspects are provided so that this disclosure will satisfy applicable legal requirements. Like numbers refer to like elements throughout.

Particular aspects of the present disclosure, as shown, for example, in FIGS. 1A and 1B provide a splint device 100 for use with a guidance system of a surgical robot, for instance, in dental surgery. One skilled in the art, however, will appreciate that the concept of the splint device disclosed herein as forming a fiducial marker and/or a tracking marker, or otherwise a frame of reference for a surgical robotic system may find applicability to other surgical processes not involving dental surgery, such as, for example, orthopedic surgery, ENT surgery, and neurosurgery. As such, the aspects of the disclosure presented herein are merely examples of the applicability of the disclosed concepts and are not intended to be limiting in any manner. That is, aspects of the splint device disclosed herein may be otherwise applicable to various parts of the patient to facilitate other types of surgery, besides dental surgery. As disclosed herein, aspects of the splint device 100 are particularly described and illustrated as being applicable to partially or fully edentulous patients for providing a surgical splint for facilitating guided robotic dental surgery, though one skilled in the art will appreciate that the splint concepts associated with these aspects may be otherwise applicable to various parts of the patient to facilitate other types of surgery, besides dental surgery.

Such a splint device 100, for example, for fully or partially edentulous patients, and implemented in conjunction with a guided surgical robot may comprise an arcuate splint body 200 having opposed first and second ends 200A, 200B and a concave surface 300 opposing a convex surface 400. The splint body 200 further defines a plurality or series of holes spaced apart between the first and second ends 200A, 200B, wherein each hole 500 extends between the concave and convex surfaces 300, 400 (e.g., each hole 500 extends to and through the concave surface 300 and to and through the convex surface 400). A tracking portion 600 is engaged with the convex surface 400 of the splint body 200, between the first and second ends 200A, 200B of the splint body 200. In particular aspects, the tracking portion 600 is engaged with the convex surface 400 of the splint body 200, between the first and second ends 200A, 200B of the splint body 200, such that at least one of the holes 500 is disposed between the tracking portion 600 and each of the first and second ends 200A, 200B. The tracking portion 600 extends outwardly from the convex surface 400 and has a kinematic mount 700 engaged therewith.

In some aspects, in an example application such as dental surgery, at least the concave surface 300 of the arcuate splint body 200 is configured and arranged to substantially conform to a mandibular curvature or maxillary curvature of the patient anatomy. In other aspects, a separability provision 800 extends across the splint body 200 (e.g., across the convex surface 400) between two adjacent holes. In some instances, the separability provision 800 is arranged to be severable so as to facilitate adjustability of a length of the splint body 200, for example, to better conform to mandibular/maxillary curves of different dimensions. That is, the adjustability of the length of the splint body 100 via the separability provision 800 can facilitate, for example, the implementation of the splint device 100 to a variety of different size applications (e.g., adult or child's mandible/maxilla) The separability provision 800, in some aspects, comprises a reduced section thickness of the splint body 200 between adjacent holes 500, whether in relation to the concave surface 300 or the convex surface 400 of the splint body 200. In other instances, multiple severability provisions 800 can be provided along the concave surface 300 and/or the convex surface 400 of the splint body 200 to provide for multiple adjustability of the length of the splint body 200 of the splint device 100.

In some aspects, the splint body 200 and the separability provision 800 are integrally formed as a single assembly. In other aspects, the splint body 200, the separability provision 800, and the tracking portion 600 are integrally formed as a single assembly. In still other aspects, the kinematic mount 700 is integrally formed with the tracking portion 600. The kinematic mount 700, in some instances, defines a central locating receptacle 725 surrounded by three or more angularly spaced-apart protrusions 750. Such a kinematic mount 700 is generally configured to receive a complementarily-configured mount (not shown) including or engaged with a tracking provision. The tracking provision can include, for example, a physically connected (e.g., mechanical) tracking provision such as a tracking arm connected to the surgical robot. In other instances, the tracking provision can include, for example, a non-physically connected tracking provision such as an optical tracking device, a magnetic tracking device, a wireless or WiFi tracking device, an electromagnetic tracking device, an inductive tracking device, or any other form of tracking device that does not require a physical connection between the tracking provision affixed to the kinematic mount 700 and the surgical robot. In either instance, the integration of the kinematic mount 700 into the tracking portion 600 provides for repeatable engagement with the tracking provision, with interchangeable engagement between different types of tracking provisions. The integration of the kinematic mount 700 can further be accomplished, for example, through molding, machining, and or 3D printing. When formed as an integral assembly, the splint device 100 may be formed, for example, using any suitable formation procedure such as injection molding, casting, or machining, as necessary or appropriate.

As previously disclosed, the splint body 200 defines a plurality or series of holes spaced apart between the first and second ends 200A, 200B, wherein each hole 500 extends between the concave and convex surfaces 300, 400 (e.g., each hole 500 extends to and through the concave surface 300 and to and through the convex surface 400), and wherein the tracking portion 600 is engaged with the convex surface 400 of the splint body 200, between the first and second ends 200A, 200B of the splint body 200, such that at least one of the holes 500 is disposed between the tracking portion 600 and each of the first and second ends 200A, 200B. In some aspects, the holes 500 immediately on either side of the tracking portion 600 are substantially equidistantly spaced therefrom.

In some aspects, each hole 500 along the splint body 200 is arranged to receive a sleeve 550 therein. The sleeves 550, in some instances, are comprised of a durable material such as, for example, a metallic material or a ceramic material. In this manner, for instance, the sleeves 550 may be arranged as a drill guide for drilling a pilot hole, for example, in the mandible/maxilla (i.e., the splint body 200 is placed against the mandible/maxilla in a dental procedure, and the pilot hole(s) are drilled with an appropriate drill bit through the corresponding sleeve(s) 550 disposed within the corresponding hole(s) 500). Once the pilot hole(s) are drilled in the mandible/maxilla, a fastener (not shown) such as a fixation screw can be advanced through the sleeve(s) 550 (e.g., the sleeve 550 is arranged as a fastener guide) and into the pilot hole(s) in the mandible/maxilla to secure the splint body 200 in place on the patient's mandible/maxilla. One skilled in the art will appreciate that the sleeves 550 are optional, in that the holes 500/splint body 200 themselves may be configured and arranged to accomplish the function and/or purpose of the sleeves 550 with respect to a drill guide and/or fastener guide as disclosed herein. In any instance, the splint device 100 is secured to the mandible/maxilla in a dental procedure by way of the disclosed fasteners.

In some instances, a tool calibration provision 1000 is engaged with the splint body 200 or the tracking portion 600, wherein the tool calibration provision 1000 is disposed in a predetermined disposition relative to the kinematic mount 700. The tool calibration provision 1000 may be configured, for example, as a receptacle or other suitable surface feature for receiving the end effector (e.g., a tip of a drill bit) of a surgical instrument affixed to the surgical robot. The tool calibration provision 1000, in some instances, is formed integrally with the particular component of the splint device 100 or, in other instances, can be a separate and discrete element (e.g., a durable element such as a metal element, a ceramic element, or other suitable element). Since the tool calibration provision 1000 is in a known disposition relative to the kinematic mount 700, the tool calibration provision 1000, upon interaction with the end effector of the surgical robot, provides a confirmation or calibration that the end effector is accurately tracked in relation to the surgical robot for conducting a procedure. In some instances, the tool calibration provision 1000 is radiopaque such that the disposition thereof with respect to the kinematic mount 700 can be determined and/or confirmed through imaging analysis.

In yet other instances, a fiducial marker element 900 (see, e.g., FIG. 1B) is received by a depression (not shown) defined by an outer surface (e.g., the convex surface 400) of the splint body 200 or the tracking portion 600, wherein the fiducial marker element 900 is received in a predetermined disposition relative to the kinematic mount 700. In particular aspects, the outer surface of the splint device 100 defines a plurality of depressions arranged to receive a corresponding plurality of fiducial marker elements 900. For example, in some aspects, the fiducial marker element 900 is spherical and the depression is hemispherical or an elongate concave channel arranged to receive the spherical fiducial marker element 900. Once secured with the respective depression, whether through an interference fit (e.g., a press fit), by overmolding, or with an adhesive material (e.g., epoxy) disposed with the depression, the fiducial marker element(s) 900 are essentially embedded within the splint device 100. Moreover, in some aspects, the depressions are oriented such that the adhesive material (e.g., epoxy) is retained, such as by gravity, at the location in the depression at which the fiducial marker element 900 is secured/embedded. Since the fiducial marker element(s) 900 are radiopaque in some aspects, the fiducial marker element(s) 900 can be detected through imaging analysis (e.g., a CT scan). Accordingly, in particular instances, the fiducial marker element(s) 900 are radiopaque and can be differentiated from the splint device 100 (e.g., formed of a plastic/polymeric material), the sleeves 550 (e.g., formed of a metallic or ceramic material), and the fasteners (e.g., metal) used for securing the splint device 100 to the patient. Since the fiducial marker element(s) 900 are all embedded with the splint device 100, the field of view of the imaging analysis (e.g., the CT scan) can be reduced.

Many modifications and other embodiments of the inventions set forth herein will come to mind to one skilled in the art to which these disclosed embodiments pertain having the benefit of the teachings presented in the foregoing descriptions and the associated drawings. Therefore, it is to be understood that embodiments of the invention are not to be limited to the specific embodiments disclosed and that modifications and other embodiments are intended to be included within the scope of the invention. For example, FIGS. 2A and 2B schematically illustrate a top view and a side profile view of a splint device 100 applicable, for example, to a medial portion of a maxilla or mandible of a fully or partially edentulous patients and arranged to provide a fiducial marker and/or a tracking marker for a guidance system for a surgical robot, according to one aspect of the present disclosure. As shown, such a splint device 100 is configured similarly to the embodiment shown in FIGS. 1A and 1B, with the splint body 200 configured to extend substantially symmetrically about an arc in each direction from a center line toward the first and second ends 200A, 200B. Thus, the center line of the splint body 200 is configured to be applied to the medial portion of the mandible with the first and second ends 200A, 200B extending substantially similarly in either direction about the mandible. In addition, the tracking portion 600 extends from a medial portion of the convex surface 400 of the splint body 200. Moreover, though not particularly described here, the embodiment illustrated in FIGS. 2A and 2B can include the enumerated elements previously described in relation to FIGS. 1A and 1B, even if not particularly illustrated, as will be understood by a person of skill in the art. Several of those enumerated elements are indicated in FIGS. 2A and 2B.

FIG. 2C schematically illustrates a splint device according to the aspect of the disclosure shown in FIGS. 2A and 2B, wherein a first one of such a splint device 100A is applied to the mandible and a second one of such a splint device 100B is inverted and applied to the maxilla. Of further note in regard to the embodiment shown in FIGS. 2A and 2B is the obtuse angle defined between the splint body 200 and the tracking portion 600. In this regard, as applied to the mandible or the maxilla, as shown in FIG. 2C, the obtuse angle allows for the tracking portion 600 to clear the patient's (lower or upper) lip upon installation of the splint body 200 to the mandible or the maxilla. For example, such a configuration of the splint device would allow the patient to close their mouth and lips about the tracking portion 600 instead of the lips remaining parted.

FIGS. 3A and 3B schematically illustrate a top view and a bottom view of a splint device 100 applicable, for example, to a medial portion of a maxilla of a fully or partially edentulous patients and arranged to provide a fiducial marker and/or a tracking marker for a guidance system for a surgical robot, according to still another aspect of the present disclosure. More particularly, due to the particular soft tissue anatomy about the maxilla (e.g., the nasal spine extending between the upper lip and the gum about the medial portion of the maxilla), the splint body 200 of the embodiment shown in FIGS. 3A and 3B includes and defines a concave relief portion 200C about the medial portion of the splint body 200 (e.g., medially between the first and second ends 200A, 200B) which is arranged to receive and accommodate the nasal spine therein. The concave relief portion 200C thus provides for a more comfortable splint device 100 in procedures involving the maxilla.

In other respects, the embodiment shown in FIGS. 3A and 3B is similar to the embodiment shown in FIGS. 2A and 2B and, even though indicated as being particularly applicable to the maxilla, can also be inverted and applied to the mandible as will be understood by a person of skill in the art. Also, the embodiment shown in FIGS. 3A and 3B can also include the obtuse angle defined between the splint body 200 and the tracking portion 600 according to the embodiment shown in FIGS. 2A and 2B, if necessary or desired. In addition, though not particularly described here, the embodiment illustrated in FIGS. 3A and 3B can include the enumerated elements previously described in relation to FIGS. 1A-B and 2A-B, even if not particularly illustrated, as will be understood by a person of skill in the art. Several of those enumerated elements are indicated in FIGS. 3A and 3B. FIGS. 3C and 3D schematically illustrate a splint device 100 according to the aspect of the disclosure shown in FIGS. 3A and 3B, applied to a maxilla.

Moreover, although the foregoing descriptions and the associated drawings describe example embodiments in the context of certain example combinations of elements and/or functions, it should be appreciated that different combinations of elements and/or functions may be provided by alternative embodiments without departing from the scope of the disclosure. In this regard, for example, different combinations of elements and/or functions than those explicitly described above are also contemplated within the scope of the disclosure. Although specific terms are employed herein, they are used in a generic and descriptive sense only and not for purposes of limitation.

It should be understood that although the terms first, second, etc. may be used herein to describe various steps or calculations, these steps or calculations should not be limited by these terms. These terms are only used to distinguish one operation or calculation from another. For example, a first calculation may be termed a second calculation, and, similarly, a second step may be termed a first step, without departing from the scope of this disclosure. As used herein, the term "and/or" and the "/" symbol includes any and all combinations of one or more of the associated listed items.

As used herein, the singular forms "a", "an" and "the" are intended to include the plural forms as well, unless the context clearly indicates otherwise. It will be further understood that the terms "comprises", "comprising", "includes", and/or "including", when used herein, specify the presence of stated features, integers, steps, operations, elements, and/or components, but do not preclude the presence or addition of one or more other features, integers, steps, operations, elements, components, and/or groups thereof. Therefore, the terminology used herein is for the purpose of describing particular embodiments only and is not intended to be limiting.

That which is claimed:

1. A splint device for guided robotic surgery, said device comprising:
    an arcuate splint body having first and second ends and opposing concave and convex surfaces, the splint body defining a plurality of holes spaced apart between the first and second ends, each hole extending between the concave and convex surfaces;
    a tracking portion engaged with the convex surface of the splint body between the first and second ends such that at least one of the holes is disposed between the tracking portion and the first end, and at least one of the holes is disposed between the tracking portion and the second end, the tracking portion extending outwardly from the convex surface and having a kinematic mount engaged therewith; and
    a fiducial marker element received by a depression defined by an outer surface of the splint body or the tracking portion, the fiducial marker element being received in a predetermined disposition relative to the kinematic mount.

2. The device of claim 1, wherein each hole is arranged to receive a sleeve therein.

3. The device of claim 2, wherein the sleeve is comprised of a metallic material or a ceramic material.

4. The device of claim 2, wherein the sleeve is arranged as a drill guide or a fastener guide.

5. The device of claim 1, wherein the kinematic mount is integrally formed with the tracking portion.

6. The device of claim 1, comprising a separability provision extending across the splint body between adjacent holes, wherein the separability provision is arranged to be severable so as to facilitate adjustability of a length of the splint body.

7. The device of claim 6, wherein the separability provision comprises a reduced section thickness of the splint body between adjacent holes.

8. The device of claim 1, wherein the fiducial marker element is spherical and the depression is hemispherical or an elongate concave channel arranged to receive the spherical fiducial marker element.

9. The device of claim 1, comprising a tool calibration provision engaged with the splint body or the tracking portion, the tool calibration provision being disposed in a predetermined disposition relative to the kinematic mount.

10. The device of claim 1, wherein the concave surface of the splint body is arranged to conform to a mandibular curvature or a maxillary curvature.

* * * * *